United States Patent [19]
Bratton

[11] Patent Number: 5,587,538
[45] Date of Patent: Dec. 24, 1996

[54] DOWNHOLE VOLATILE ORGANIC COMPOUNDS TRAP FOR IMPROVED SAMPLING OF VOLATILE ORGANIC COMPOUNDS USING CONE PENETROMETER TESTING TECHNIQUES

[75] Inventor: Wes Bratton, South Royalton, Vt.

[73] Assignee: Applied Research Associates, Inc., Albuquerque, N.M.

[21] Appl. No.: 540,802

[22] Filed: Oct. 11, 1995

[51] Int. Cl.$^6$ ......................................... G01N 1/16
[52] U.S. Cl. ........................ 73/863.33; 73/864.74
[58] Field of Search ................................ 73/155, 864.74, 73/863.11, 863.23, 863.31, 863.33

[56] References Cited

U.S. PATENT DOCUMENTS

| | | |
|---|---|---|
| 2,959,397 | 11/1960 | Gardner et al. . |
| 3,929,411 | 12/1975 | Takano et al. ............... 23/259 |
| 4,310,057 | 1/1982 | Drame . |
| 4,807,707 | 2/1989 | Handley et al. . |
| 4,999,164 | 3/1991 | Puchinger et al. ............. 73/863.23 |
| 5,007,488 | 4/1991 | Donovan . |
| 5,035,149 | 7/1991 | Wierenga . |
| 5,146,998 | 9/1992 | Cordry et al. . |
| 5,150,622 | 9/1992 | Vollweiler . |
| 5,297,954 | 3/1994 | Colagiovanni ................ 431/5 |
| 5,337,838 | 8/1994 | Sorensen . |
| 5,381,699 | 1/1995 | Dansereau et al. ............ 73/863.23 |

*Primary Examiner*—Richard Chilcot
*Assistant Examiner*—Max H. Noori
*Attorney, Agent, or Firm*—Jacobson, Price, Holman & Stern, PLLC

[57] ABSTRACT

Three separate volatile organic compound (VOC) traps are installed in a housing driven into the earth using cone penetrometer testing (CPT) techniques. The traps are valved so that each trap is filled at a different depth. Operation of the unit is done by installing three fresh clean traps into a cone module. The unit is pushed to the desired depth using CPT techniques. One of the three traps is selected using an electronic switch in a truck located above the collection site to control a valving arrangement for direction of VOCs to a selected trap. Heaters are turned on to heat the surrounding soil to increase removal of volatiles from the soil or water at the sample collection point. The heaters are formed of nickel-chromium wires wrapped around an insulated section of the CPT push rod. The wire is protected during the penetration process by a stainless steel sleeve that threads over the wire wrapped section. Electricity through the wire will heat the wire to approximately 200° Celsius which will then heat the surrounding soil. The VOC trap collects the volatiles downhole thereby eliminating any possibility of volatilization during the recovery and testing process.

20 Claims, 2 Drawing Sheets

DOWNHOLE VOLATILE ORGANIC COMPOUNDS TRAP FOR IMPROVED SAMPLING OF VOLATILE ORGANIC COMPOUNDS USING CONE PENETROMETER TESTING TECHNIQUES

FIELD OF THE INVENTION

The invention allows volatile organic compounds (VOC) to be collected downhole in a VOC trap using cone penetrometer testing (CPT) techniques.

BACKGROUND OF THE INVENTION

The Environmental Protection Agency (EPA) has recently realized that nearly 80% of the VOCs they are attempting to measure during site investigations are escaping from the sample prior to analysis. The possible sources of VOC escape are (1) during the sampling process, and (2) during the sampling holding time prior to analysis.

Sampling is currently being accomplished by attaching a vacuum pump to plastic tubing running to a filtering point at a given depth. Soil gas samples are drawn through the tubing and into gas sample bags. Locations of VOC loss are (1) through the plastic tubing, (2) through the sample bag walls, and (3) through any fittings. To improve the system and reduce the possible locations of leaks, both the sampling transport mechanisms to the laboratory and the sampling procedure need to be improved.

Currently, measurements of some sample properties are made prior to bringing the sample to the surface. Samples potentially change characteristics during the process of bringing them to the surface and the subsurface measurements purportedly allow corrections to be made to the surface measurements by comparisons to the subsurface measurements. However, all measurements necessary to determine the total nature of the sample cannot be made downhole so the accuracy of the corrections is conjectural. In addition, it is now common to have loss of volatiles from the sample in all current sampling devices.

SUMMARY OF THE INVENTION

To improve the sampling procedure according to the present invention, the sample collection unit is moved as close as possible to the collection point to reduce VOC loss in the fittings and the tubing. To improve the sample collection unit of the present invention, a purge and trap analysis trap is used to hold the sample prior to analysis. These two improvements are implemented in a VOC trap collection cone penetration sampler probe according to the principles of the present invention.

By the present invention, three separate 30 centimeter long, 0.3 inch diameter VOC traps are installed in a cone penetrometer. The traps are valved such that each trap is filled at a different depth.

Operation of the unit is done by installing three fresh clean traps into a cone module. The unit is pushed to the desired depth using cone penetration testing techniques. One of the three traps is selected using an electronic switch in a truck located above the collection site to control a valving arrangement for direction of VOCs to a selected trap. Heaters are turned on to heat the surrounding soil to increase removal of volatiles from the soil or water at the sample collection point.

The heaters are formed of nickel-chromium wires wrapped around an insulated section of the CPT push rod. The wire is protected during the penetration process by a stainless steel sleeve that threads over the wire wrapped section. Electricity through the wire will heat the wire to approximately 200° Celsius which will then heat the surrounding soil.

The VOC trap collects the volatiles downhole thereby eliminating any possibility of volatilization during the recovery and testing process. Additionally, the present invention will do multiple samples per penetration.

A vacuum pump is started and sampling begins for a set amount of time. After the desired time, the vacuum pump is turned off along with the heaters. The valves of the valving arrangement are rotated by a miniature solenoid valve to a neutral position, sealing the used trap. The cone module is advanced to the next depth and the process repeated. The solenoid valves are used within the probe to control the directions and routing of gaseous samples downhole.

After all traps are used, the unit is retrieved and the traps removed and sealed and sent to an analytical laboratory for purge and trap gas chromatograph analysis. Once the analytical laboratory is ready to analyze the sample, the traps are installed in a purge and trap unit and standard analysis begins.

These procedures work for sampling in the vadose zone. To perform VOC sampling below the water table, the operation is very similar, except additional steps are required.

As before, three new traps are installed and the unit pushed to the desired depth. At this depth a porous filter is exposed by pulling back on the cone rod housing. This allows water to flow into the sampling cavity. If water flow is slow, a vacuum pump is activated to increase the speed of the process.

After enough water has entered the sampling chamber, the sample is purged with helium gas carrying the VOCs from the water into the trap. After a set amount of purging has occurred, the valves are rotated to a neutral position, sealing the sample. The sampling chamber is flushed with a methanol/water solution and then two chamber volumes of clean water. The chamber is dried using air flow through the chamber. Finally the filter is closed by return of the housing and the probe advanced to the next depth of interest. After all traps are used or all desired depths have been sampled, the unit is returned to the surface and the traps removed and sealed. Finally, the traps are sent to a laboratory for analysis.

The sampling chamber can also be used with many other water sampling sensors such as pH, conductivity, chemical sensors, etc., and it is not intended to be limited to the VOC sampler.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
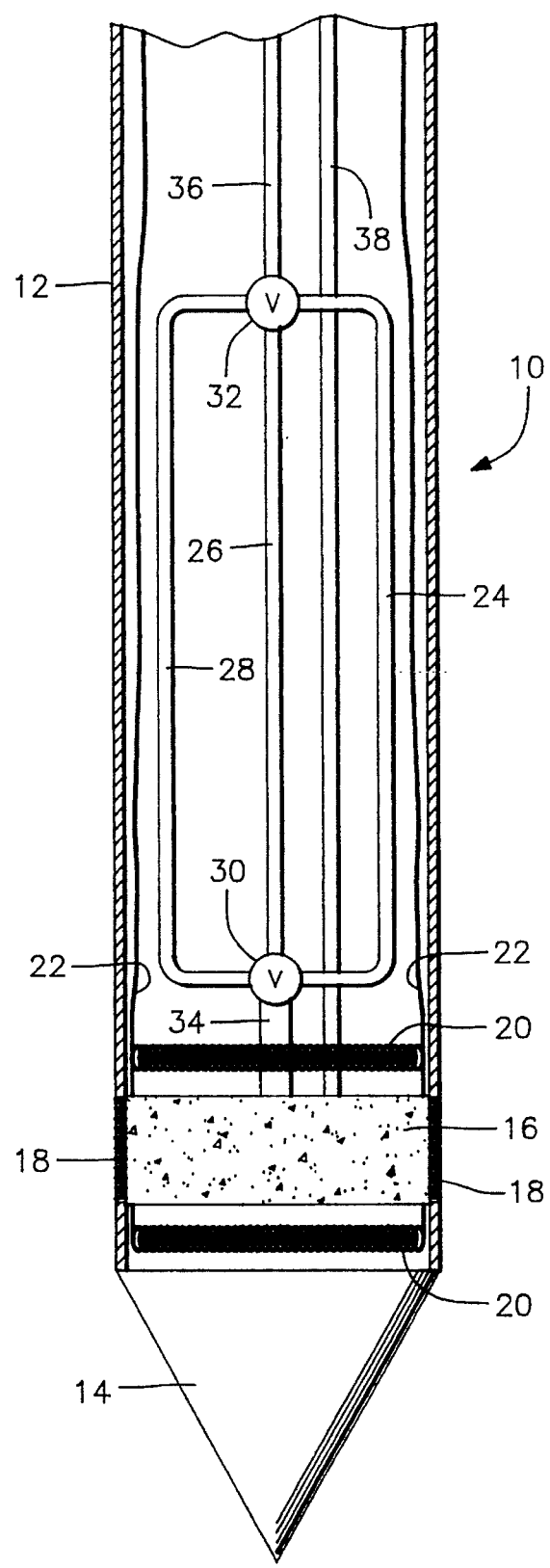
FIG. 1 is a sectional view of a VOC trap collection cone penetration sampler probe having a filter for sampling VOCs.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general, and to FIG. 1, in particular, a downhole VOC trap collection cone penetration sampler probe for sampling volatile organic compounds using cone penetrometer testing techniques, embodying the teachings of the subject invention is generally designated as 10. CPT techniques are governed by ASTM standard D-3441 "Standard Test Method for Deep, Quasi-Static, cone and Friction-Cone Penetration Tests of Solid". CPT is a geotechnical technique for determining soil strength parameters of near surface soils to depths of approximately 300 feet. CPT uses hydraulically operated rams mounted on a specifically designed truck to push various measurement probes into the soil. One meter long threaded, hollow steel pipe sections are used to incrementally lengthen the pushing stem. Electrical cables attached to the measurement probes are threaded through the hollow pipes and connected to electronic data acquisition and analysis equipment in the truck.

During the penetration process, the forces required to advance the probe are recorded on the data acquisition system. This provides a continuous record of the soil parameters during the testing process.

By the present invention, CPT is used in combination with a VOC trap as a sample container. In the embodiment shown in FIG. 1, the probe 10 includes a housing 12 formed of hollow rod, terminating in a cone 14 having side walls converging at an angle of 60°.

At an end of the housing 12, adjacent to the cone 14, is a porous filter 16 for sampling VOCs. VOCs are allowed to migrate into the housing through openings 18 in the sidewall of the housing. Positioned above and below the filter 16 are heater units 20 connected by wires 22 to an above-ground location for control of the heating of the sidewall and the exterior of the housing 12.

Located within the housing are three VOC traps 24, 26, and 28. A lowermost end of each trap is commonly connected to a valve 30 and an uppermost end of each trap is also commonly connected to a valve 32. Valve 30 is connected to a conduit 34 which extends into porous filter 16 so as to convey VOCs entering the filter 16 to the valve 30. Valve 32 is connected to a vacuum line 36 which extends to the surface and is controlled for exerting a vacuum force to valve 32 and beyond valve 32, dependent upon the position of valves 30 and 32. A flushing line 38 extends from above ground and communicates with filter 16 for cleaning the filter with either air or water from the surface.

In operation, valves 30 and 32 are controlled from the surface, either electrically or by remote control signals, to vary the position of the valves for obtaining and sealing a VOC sample within the traps 24, 26 or 28. Each of the three traps can thereby be filled with a VOC sample at different depths of penetration as allowed for by the use of CPT techniques.

After initial flushing of the filter 16 by air or water from flush line 38, vacuum line 36 is activated and valves 30 and 32 rotated so as to provide a vacuum force through one trap, for example trap 24, to communicate trap 24 with the vacuum line 36 and the conduit 34 so as to exert a vacuum on the filter 16. A VOC sample is thereby brought through filter 16, conduit 34, and into trap 24 by the force of the vacuum exerted from vacuum line 36 until the valves 30 and 32 are rotated to seal the VOC contents in trap 24 from further communication with the conduit 34 and the vacuum line 36.

Continued penetration of the probe 10 to a second selected depth is then performed. The filter 16 can be flushed with either air or water from flushing line 38 to provide clear communication with the surrounding environment. The valves 30, 32 are rotated to obtain a sample in a second trap, for example trap 26, by communicating the vacuum line 36 with trap 26 and conduit 34 to exert a vacuum force to the exterior of the housing so as to obtain a VOC sample through filter 16. Rotation again of the valves 30, 32 seals a VOC sample in the trap 26.

Continued penetration of the probe 10 to a third depth is performed to obtain a third sample in the third trap 28 in a similar matter as was described with respect to traps 24 and 26. Selective energization of the heater units 20 increases removal of volatiles from the soil or water at the sample collection point at each of the selected depths of penetration performed according to CPT techniques.

If sampling is desired below the vadose zone, and in the water table, the embodiment shown in FIG. 2 and 3 would be used. This embodiment operates in a similar matter to the embodiment shown in FIG. 1.

Figure 2:
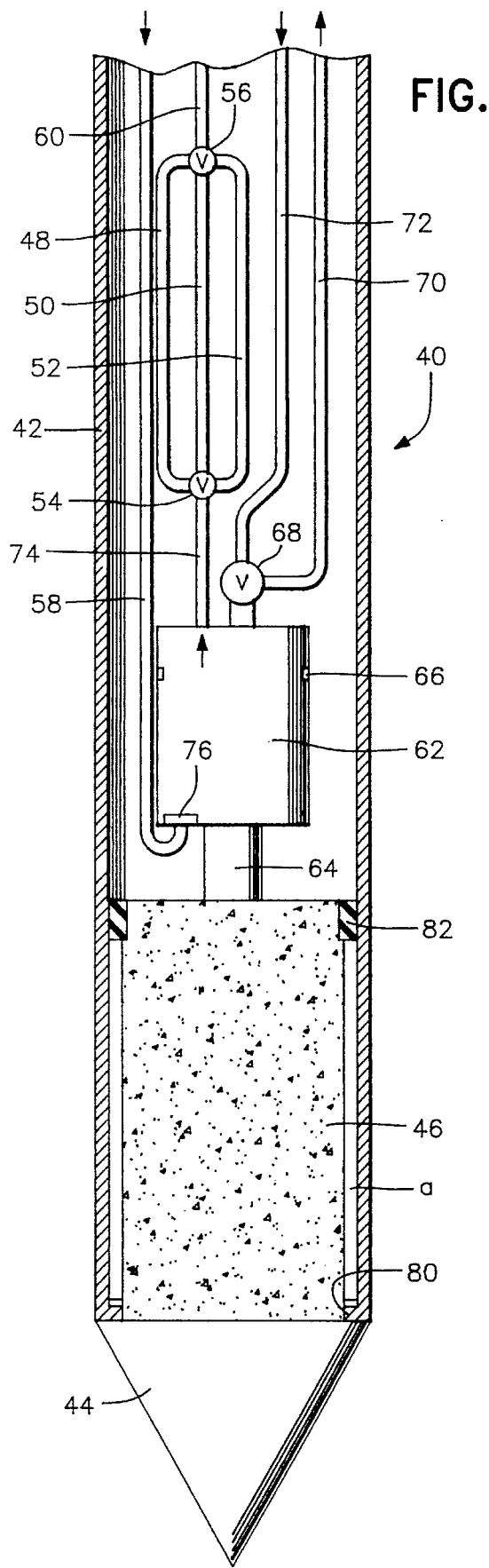
FIG. 2 is a sectional view of an alternative embodiment of a VOC trap collection cone penetration sampler probe for sampling VOCs below the water table.

In FIG. 2, probe 40 is shown having housing 42 formed of a cylindrical rod. The housing 42 terminates in cone 44 having side walls converging at an angle of 60°. Adjacent to the cone is a porous filter 46 spaced slightly radially inwardly from the interior sidewall of the housing 42 by a gap "a".

As in FIG. 1, three traps 48, 50, 52, are connected in common to a lower valve 54 and an upper valve 56. The valves 54 and 56 control the inputting of samples through conduit 58 into the traps by a force exerted from vacuum line 60, dependent upon the position of the valves 54 and 56. The conduit 58 which introduces samples into the traps 48, 50 or 52, is connected to a sampling chamber 62 having a pipe 64 communicating with the sampling chamber and the filter 46.

Figure 3:
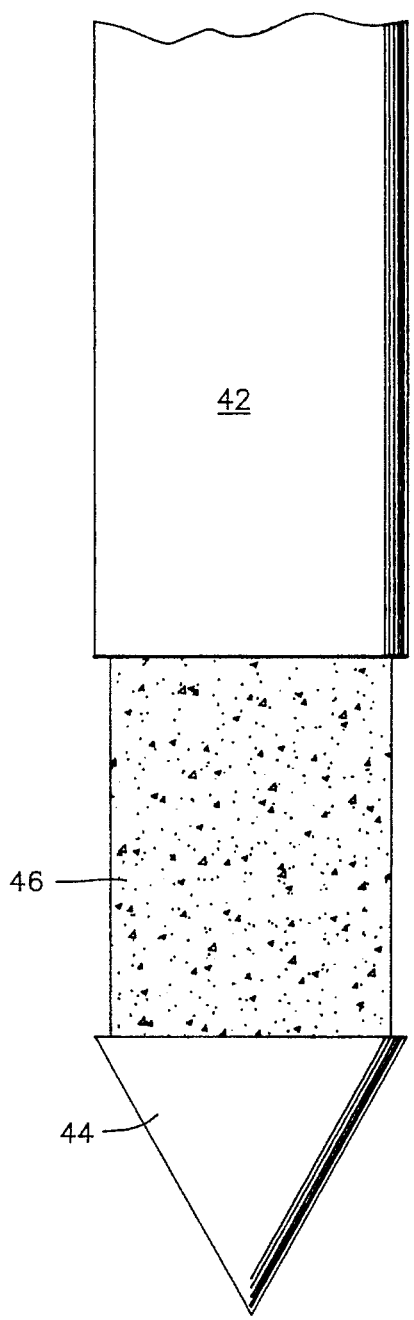
FIG. 3 is a side view of the sampler probe shown in FIG. 2, with a porous filter exposed by pulling back on the cone rod or housing.

To allow a sample to enter through the porous filter 46, the housing 42 is withdrawn away from the cone 44, to an "open" position as shown in FIG. 3, until the radially inwardly extending flange 80 encounters annular stop ring 82. VOCs are thereby allowed to enter with water through the filter 46 into the sampling chamber 62. At a predetermined depth of penetration of the probe 40, the housing is withdrawn to allow water to enter the sampling chamber 62 through the filter 46. If the water level rises in the sampling chamber too slowly, the vacuum line 70 is activated to increase the speed of the process.

After enough water has entered the sampling chamber, as indicated by the actuation of water indicator ring 66, the sample is obtained by allowing helium to flow through helium conduit 74 into the bottom of the sampling chamber 62 through frit 76 at the bottom of the sampling chamber. The helium gas carries the VOC samples from the water in the sampling chamber into the trap selected by the valves 54, 56.

The sampling chamber is then flushed with a methanol/water solution through flush line 72, followed by two chamber volumes of clean water. The chamber is dried using air flow brought into the chamber through the helium flow line 74 and evacuated through the vacuum line 70. A flush/fill valve 68 is rotated to allow evacuation of air through a vacuum line 70. Alternatively, the flush-fill valve 68 is rotated for introduction of a liquid, such as water or a methanel/water solution, through flush line 72 for communication with the sampling chamber and through the pipe 64 to the filter 46.

Once a sample has been obtained, the housing is returned to its position adjacent to the cone 44, as shown in FIG. 2, and continued penetration of the soil is performed using CPT techniques until the probe reaches the next desired depth. Another sample is obtained by the raising of the housing 42 and exposing of the filter 46 and rotation of the valves 54, 56 for completion of another sampling cycle. Further testing is performed at a third depth using CPT techniques and another trap of the probe 40.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A probe for obtaining a plurality of samples of volatile organic compounds at different depths up to 300 feet, said probe comprising:

a hollow housing for penetrating the earth, and a plurality of volatile organic compound traps fixedly mounted in said housing for accompanying said housing as said housing penetrates the earth, said plurality of traps each having two ends and each end of each of said plurality of traps being connected respectively to two common valves for controlling entry of a volatile organic compound sample into a respective one of said plurality of traps dependent upon a position of said valves at each end of said plurality of traps so that a sample of volatile organic compounds under a vacuum force can be obtained at different depths of penetration of the earth by said housing.

2. A probe as claimed in claim 1, wherein said housing includes heater units for heating the earth.

3. A probe as claimed in claim 1, wherein said housing includes a cone at a leading end for driving of said housing with said traps through the earth by cone penetrometer testing techniques applied to a trailing end of said housing.

4. A probe as claimed in claim 1, wherein a cone is located at a leading end of said housing and said housing is withdrawable from said cone to expose a porous filter.

5. A probe as claimed in claim 1, wherein said housing include a porous filter adjacent to a leading end of said housing.

6. A probe as claimed in claim 5, wherein a flush line extends through said housing and communicates with said filter for passing of water to said filter and cleaning said filter to allow samples to be drawn from multiple depths in one probing.

7. A probe as claimed in claim 5, wherein one of said valves is in communication with a conduit extending from said filter for transfer of volatile organic compounds from said filter to said one valve and to one of said traps dependent upon a position of said valves.

8. A probe as claimed in claim 4, wherein said housing includes a sampling chamber located inbetween said filter and said traps in a flow of volatile organic compounds through said housing for collecting water passing through said filter when said filter is exposed.

9. A probe as claimed in claim 8, wherein a gas transfer conduit extending to an above ground location is connected to a bottom surface of said sampling chamber for introducing a gas in water contained in said sampling chamber to convey volatile organic compounds from said sampling chamber to one of said traps.

10. A probe as claimed in claim 8, wherein a flush/fill valve is in communication with said sampling container and with one of a flush line and a vacuum line.

11. A probe for obtaining a plurality of samples of volatile organic compounds at different depths up to 300 feet, said probe comprising:

a hollow housing terminating in a cone, said housing being positionable in a position of use extending from below ground level to above ground level, a porous filter located at a leading end of said housing, and a plurality of volatile organic compound traps fixedly mounted in said housing so as to accompany said housing as said housing is moved from above ground level to said position of use, each of said plurality of traps extending between two valves for controlling communication with said filter and a vacuum line so as to provide a sample of volatile organic compounds to a respective one of said traps at different depths of said housing in the earth.

12. A probe as claimed in claim 11, wherein said housing includes heater units for heating the earth.

13. A probe as claimed in claim 11, wherein a flush line is in communication with said filter for cleaning said filter with one of air and water.

14. A probe as claimed in claim 11, wherein said valves are rotatable for controlling passage to one of said traps of volatile organic compounds.

15. A probe for obtaining a plurality of samples of volatile organic compounds at different depths up to 300 feet, said probe comprising:

a hollow housing terminating in a cone, a porous filter located in said housing at a leading end of said housing, said housing being retractable from said cone to expose said filter at different depths of said housing in the earth, and a plurality of volatile organic compound traps fixedly mounted in said housing so as to accompany said housing as said housing is passed to different depths, each of said plurality of traps extending between two valves for controlling communication with said filter and a vacuum line so as to provide a sample of volatile organic compounds to a respective one of said traps at different depths of said housing in the earth.

16. A probe as claimed in claim 15, wherein one of said valves is in communication with a conduit extending from said filter for transfer of volatile organic compounds from said filter to said one valve and to one of said traps dependent upon a position of said valves.

17. A probe as claimed in claim 15, wherein said housing includes a sampling chamber located inbetween said filter and said traps in a flow of volatile organic compounds through said housing for collecting water passing through said filter when said filter is exposed.

18. A probe as claimed in claim 17, wherein a gas transfer conduit extending to an above ground location is connected to a bottom surface of said sampling chamber for introducing a gas into water contained in said sampling chamber to convey volatile organic compounds from said sampling chamber to one of said traps.

19. A probe as claimed in claim 17, wherein a flush/fill valve is in communication with said sampling container and with one of a flush line and a vacuum line.

20. A probe as claimed in claim 15, wherein aid valves are rotatable for controlling passage to one of said traps of volatile organic compounds.

* * * * *